United States Patent [19]

Psiorz et al.

[11] Patent Number: 5,147,882
[45] Date of Patent: Sep. 15, 1992

[54] CYCLOPHANES, PHARMACEUTICAL COMPOSITIONS CONTAINING THESE COMPOUNDS AND PROCESSES FOR PREPARING THEM

[75] Inventors: Manfred Psiorz, Ingelheim am Rhein; Volker Trach, Biberach, both of Fed. Rep. of Germany

[73] Assignee: Karl Thomae GmbH, Biberach an der Riss, Fed. Rep. of Germany

[21] Appl. No.: 678,556

[22] Filed: Mar. 28, 1991

[30] Foreign Application Priority Data

Apr. 2, 1990 [DE] Fed. Rep. of Germany ....... 4010531

[51] Int. Cl.$^5$ .................. A61K 31/445; C07D 211/06
[52] U.S. Cl. .................... 514/325; 546/203; 546/204; 548/528; 544/294; 544/105; 540/609; 564/230; 564/305
[58] Field of Search .............. 546/203, 204; 514/325; 540/609; 548/528; 544/294, 105

[56] References Cited

PUBLICATIONS

Upjohn Co., "Therapeutically active . . . ", CA 63: 9892d (1965).
Burger et al., "Certain physiologically . . . ", CA 62: 11750h (1965).
Hagishita et al., "Synthesis and absolute . . . ", Chem. Pharm. Bull. 24 (8) 1724-1730 (1976).

*Primary Examiner*—Alan L. Rotman
*Assistant Examiner*—Celia Chang
*Attorney, Agent, or Firm*—David E. Frankhouser; Daniel Reitenbach; Alan R. Stempel

[57] ABSTRACT

Cyclophanes of the general formula

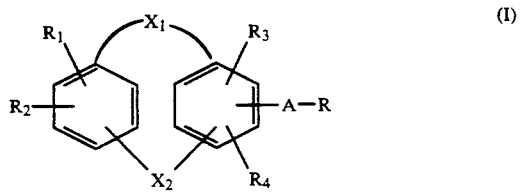

wherein $X_1$, $X_2$, A, R and $R_1$ to $R_4$ are as defined herein, the enantiomers, diastereomers and addition salts thereof and, more particularly, for pharmaceutical use, the physiologically acceptable addition salts thereof, which have pharmacological properties such as lowering blood pressure, dilating the coronary blood vessels and a mild heart rate lowering activity, pharmaceutical compositions which contain these compounds and processes for preparing them.

16 Claims, No Drawings

CYCLOPHANES, PHARMACEUTICAL COMPOSITIONS CONTAINING THESE COMPOUNDS AND PROCESSES FOR PREPARING THEM

The present invention relates to cyclophanes of general formula

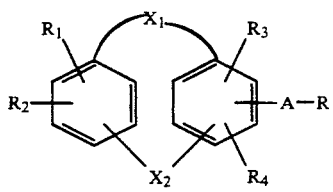

the enantiomers, diastereomers and addition salts thereof, more particularly, for pharmaceutical use, the physiologically acceptable addition salts thereof, drugs containing these compounds and processes for preparing them.

The new compounds have valuable properties, in particular useful pharmacological properties such as the effect of lowering blood pressure and dilating the coronary artery as well as a mild heart rate lowering effect.

In general formula I above $X_1$ and $X_2$, which may be identical or different, represent a straight-chained $C_{2-4}$-alkylene or alkenylene group, A represents a straight-chained $C_{1-6}$-alkylene group, a $-Y_1-A_1-$ or $-Y_2-A-$ group, wherein $Y_1$ represents an oxygen atom or a sulphenyl, sulphinyl or sulphonyl group and $A_1$ represents a straight-chained $C_{2-4}$-alkylene group, $Y_2$ represents an ethenylene or ethynylene group and $A_2$ represents a straight-chained $C_{1-3}$-alkylene group, where the groups $A_1$ and $A_2$ are linked to the group R and the carbon structure of the groups A, $A_1$ and $A_2$ may additionally be substituted by one or two methyl groups, $R_1$, $R_2$, $R_3$ and $R_4$, which may be identical or different, represent a hydrogen or halogen atom or an alkyl, hydroxy, alkoxy or alkylsulphonyloxy group each having 1 to 3 carbon atoms in the alkyl part and R represents a cyano group or a group of formula

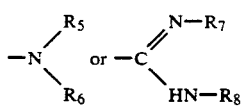

wherein $R_5$ represents a hydrogen atom, a $C_{1-10}$-alkyl group, a $C_{5-7}$-cycloalkyl group, a $C_{6-15}$-bi- or tricyclic alkyl group, whilst each of the above-mentioned cyclic groups may be substituted by one or two $C_{1-3}$-alkyl groups, or a phenylalkyl group wherein the alkyl part may contain 1 to 3 carbon atoms and the phenyl nucleus may be mono-, di- or trisubstituted by a halogen atom or by a $C_{1-3}$-alkyl or alkoxy group, $R_5$ and $R_6$ together with the nitrogen atom between them represent a pyrrolidino, piperidino, hexamethyleneimino or morpholino group, whilst i) in a piperidino or hexamethyleneimino group mentioned above in the definition of the groups $R_5$ and $R_6$, a methylene group in the 4-position may be replaced by an imino, alkylimino, alkoxycarbonylimino, alkanoylimino or phenylalkylimino group, or by a $C_{2-3}$-alkylimino group substituted by phenoxy in the 2 or 3-position, or by a phenylalkenylimino group in which the alkenyl part may contain 2 or 3 carbon atoms, or ii) a piperidino group mentioned above in the definition of groups $R_5$ and $R_6$ may be substituted by a hydroxy, alkoxy, carboxy, alkoxycarbonyl, aminocarbonyl, alkylaminocarbonyl or dialkylaminocarbonyl group or by a $C_{1-5}$ alkyl group which may be substituted by a hydroxy, alkoxy, alkanoyloxy, cyano, carboxy, alkoxycarbonyl, aminocarbonyl, alkylaminocarbonyl, dialkylaminocarbonyl, amino, alkylamino, dialkylamino, alkanoylamino, alkylsulphonylamino, N-alkanoyl-alkylamino or N-alkylsulphonyl-alkylamino group, whilst, unless otherwise specified, the alkyl, alkoxy and alkanoyl moieties mentioned above under i) and ii) may each contain 1 to 3 carbon atoms and the above-mentioned phenyl nuclei may each be monosubstituted by a nitro or trifluoromethyl group or mono-, di- or trisubstituted by halogen atoms, $C_{1-3}$-alkyl groups or $C_{1-3}$-alkyloxy groups, and the substituents may be identical or different, and $R_7$ and $R_8$, which may be identical or different, represent hydrogen atoms or $C_{1-3}$-alkyl groups.

However, the preferred compounds are the [2.2]paracyclophanes of general formula

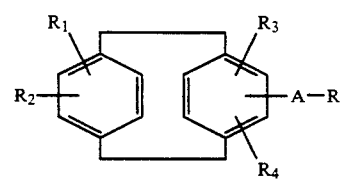

wherein

A represents a straight-chained $C_{1-5}$-alkylene group, a $-Y_1-A_1-$ or $-Y_2-A_2-$ group wherein $Y_1$ represents an oxygen atom and $A_1$ represents a straight-chained $C_2$ or $C_3$-alkylene group, $Y_2$ represents an ethenylene or ethynylene group and $A_2$ represents a methylene group, the groups A and $A_2$ being linked to the group R, one of the groups $R_1$, $R_2$, $R_3$ or $R_4$ represents a hydrogen, fluorine, chlorine or bromine atom or a methyl, hydroxy, methoxy or methanesulphonyloxy group and the other groups $R_1$, $R_2$, $R_3$ or $R_4$ each represents a hydrogen group or a methyl group, and R represents a cyano group or a group of the formula

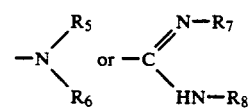

wherein $R_5$ represents a hydrogen atom, a $C_{1-3}$-alkyl group optionally substituted by a phenyl or dimethoxyphenyl group, a $C_{4-8}$-alkyl group, a $C_{5-7}$-cycloalkyl group or a $C_{7-12}$-bi- or tricyclic alkyl group, whilst each of the above-mentioned cyclic groups may be substituted by one or two methyl groups, $R_6$ represents a hydrogen atom or a $C_{1-3}$-alkyl group or R₅ and R₆ together with the nitrogen atom between them represent a pyrrolidino, piperidino, hexamethyleneimino or morpholino group, whilst i) in a piperidino or hexamethyleneimino group mentioned above in the definition of groups R₅ and R₆ a methylene group in the 4-position may be replaced by an imino, methylimino, ethoxycarbonylimino, acetylimino, phenylethylimino, phenoxyethylimino or phenylallylimino group, or ii) a piperidino group mentioned above in the definition of groups R₅ and R₆ may be substituted by a carboxy, ethoxycarbonyl, aminocarbonyl, methylaminocarbonyl or dimethylaminocarbonyl group or by a methyl group substituted by a hydroxy, acetoxy, cyano, carboxy, ethoxycarbonyl, aminocarbonyl, methylaminocarbonyl, dimethylaminocarbonyl, amino, methylamino, dimethylamino, diethylamino, acetylamino, N-acetylmethylamino, methanesulphonylamino or N-methanesulphonyl-methylamino group or by an ethyl group substituted in the 2-position by a hydroxy, carboxy or ethoxycarbonyl group or by a C₂₋₄-alkyl group substituted in a 2-, 3- or 4-position by a dimethylaminocarbonyl group, whilst, unless otherwise specified, the phenyl nuclei mentioned under i) and ii) hereinbefore may each be monosubstituted by a nitro or trifluoromethyl group or mono-, di- or trisubstituted by methyl or methoxy groups and the substituents may be identical or different, and R₇ and R₈, which may be identical or different, represent hydrogen atoms or methyl groups, the enantiomers, diastereomers and addition salts thereof, more particularly for pharmaceutical use the physiologically acceptable addition salts thereof.

Particularly preferred compounds of general formula Ia are those wherein

A represents a straight-chained C₂₋₄-alkylene group, a —Y₁—A₁— or —Y₂—A₂— group, wherein Y₁ represents an oxygen atom and A₁ represents a straight-chained C₂ or C₃-alkylene group, Y₂ represents an ethenylene or ethynylene group and A₂ represents a methylene group, the groups A₁ and A₂ being linked to the group R, R₁, R₂, R₃ and R₄ each represents a hydrogen atom and R represents a group of formula

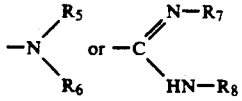

wherein R₅ represents a hydrogen atom, a C₁₋₃-alkyl group optionally substituted by a phenyl or dimethoxyphenyl group, a C₄₋₈-alkyl group, a C₅₋₇-cycloalkyl group or a bi- or tricyclic C₇₋₁₂-alkyl group, whilst each of the above-mentioned cyclic groups may be substituted by one or two methyl groups, R₆ represents a hydrogen atom or a C₁₋₃-alkyl group or R₅ and R₆ together with the nitrogen atom between them represent a piperidino group, whilst i) in a piperidino group mentioned hereinbefore in the definition of the groups R₅ and R₆, a methylene group in the 4-position may be replaced by an imino, methylimino, ethoxycarbonylimino, acetylimino, phenylethylimino, phenoxyethylimino or phenylallylimino group or ii) a piperidino group mentioned above in the definition of groups R₅ and R₆ may be substituted in the 3- or 4-position by a carboxy, ethoxycarbonyl, aminocarbonyl, methylaminocarbonyl or dimethylaminocarbonyl group or by a methyl group substituted by hydroxy, acetoxy, cyano, carboxy, ethoxycarbonyl, aminocarbonyl, methylaminocarbonyl, dimethylaminocarbonyl, amino, methylamino, dimethylamino, diethylamino, acetylamino, N-acetylmethylamino, methanesulphonylamino or N-methanesulphonyl-methylamino or by an ethyl group substituted in the 2-position by a hydroxy, carboxy or ethoxycarbonyl group, or by a C₂₋₄-alkyl group substituted in a 2-, 3- or 4-position by a dimethylaminocarbonyl group, whilst, unless otherwise specified, the phenyl nuclei mentioned under i) and ii) may each be monosubstituted by a methyl, nitro or trifluoromethyl group or mono-, di- or trisubstituted by methoxy groups, and R₇ and R₈ each represent a hydrogen atom or a methyl group, the enantiomers, diastereomers and addition salts thereof, more particularly for pharmaceutical use the physiologically acceptable addition salts thereof.

According to the invention, the new compounds are obtained by the following methods:

a) reacting a compound of general formula

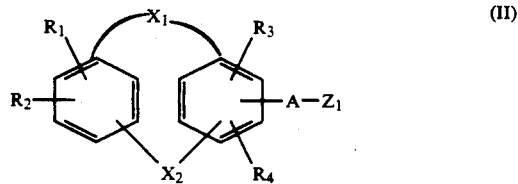

wherein

R₁ to R₄, X₁, X₂ and A are as hereinbefore defined and

Z₁ represents a nucleophilic leaving group such as a halogen atom, e.g. a chlorine, bromine or iodine atom, or a substituted sulphonyloxy group, e.g. a methanesulphonyloxy, phenylsulphonyloxy or p-toluenesulphonyloxy group, with an amine of general formula

H—R (III)

wherein R is as hereinbefore defined, or with an alkali metal salt thereof and, in order to prepare a corresponding amidino compound of general formula I, subsequently converting a cyano compound of general formula I thus obtained via the iminoester thereof, with an amine of general formula

R₇—NH₂ (IV)

wherein R₇ is as hereinbefore defined.

The reaction is conveniently carried out in a solvent or mixture of solvents such as methylene chloride, diethylether, tetrahydrofuran, dioxan, dimethylsulphoxide or benzene, optionally in the presence of an acid binding agent, such as sodium carbonate, potassium carbonate, sodium hydroxide, potassium tert.butoxide, triethylamine or pyridine, whilst the latter two may simultaneously also be used as solvents, preferably at temperatures between 0° and 100° C., e.g. at temperatures between ambient temperature and the boiling temperature of the reaction mixture.

The subsequent conversion of a resulting cyano compound into a corresponding amidino compound is preferably carried out in a solvent such as diethylether, tetrahydrofuran, dioxan or methanol/diethylether at temperatures between 0° and 20° C., the corresponding iminoester being prepared, optionally under protective gas, e.g. nitrogen, first of all by means of an alcoholic hydrochloric acid which is obtained for example by adding hydrogen chloride to absolute methanol/diethylether, and this iminoester is then converted into the corresponding amidine with an amine of formula IV in a solvent such as methanol or diethylether/$R_7$—$NH_2$ at 0° C.

b) In order to prepare a compound of general formula I where R does not represent a cyano, amidino or guanidino group and $Y_1$ does not represent a sulphinyl or sulphonyl group and the group R does not contain a carbonyl function:

Reducing a compound of general formula

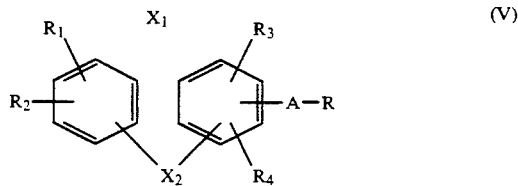

wherein R and A are as hereinbefore defined, but in A, $A_1$ or $A_2$ a —$CH_2$— group adjacent to the group R must be replaced by a —CO—group or an adjacent —$CH_2$—$CH_2$—group must be replaced by a —CO—CO— group, with a complex metal hydride.

The reduction is preferably carried out in a suitable solvent such as diethylether or tetrahydrofuran and optionally under protective gas, e.g. under nitrogen, in the presence of a metal hydride, such as lithium aluminium hydride, diborane or borane/dimethylsulphide at between 0° and 80° C., but preferably at the boiling temperature of the reaction mixture.

During the reduction, any carbonyl function present in the group R will simultaneously be reduced.

In the reactions described above, any reactive groups present such as hydroxy, amino, imino or alkylamino groups may be protected during the reaction with conventional protective groups which are split off again after the reaction has ended.

Suitable protective groups for a hydroxy group include, for example, the trimethylsilyl, acetyl, benzoyl, methyl, ethyl, tert.butyl, benzyl and tetrahydropyranyl groups and suitable protective groups for an amino, alkylamino or imino group include the acetyl, benzoyl, ethoxycarbonyl or benzyl group.

The optional subsequent splitting off of any protecting group which may be used is preferably carried out by hydrolysis in an aqueous solvent, e.g. in water, isopropanol/water, tetrahydrofuran/water or dioxane/water, in the presence of an acid such as hydrochloric or sulphuric acid or in the presence of an alkali metal base such as sodium hydroxide or potassium hydroxide at temperatures of between 0° and 100° C., preferably at the boiling temperature of the reaction mixture. However, a benzyl group is preferably split off by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures between 0° and 50° C., but preferably at ambient temperature, and under a hydrogen pressure of 1 to 7 bar, but preferably from 3 to 5 bar.

If according to the invention a compound of general formula I is obtained wherein R contains an alkoxycarbonyl group, this can be converted by hydrolysis into a corresponding hydroxycarbonyl compound of general formula I, whilst at the same time a hydroxycarbonylimino or hydroxycarbonylamino compound of general formula I formed in the reaction mixture is decarboxylated during heating to form the corresponding imino or amino compound of general formula I, or if a compound of general formula I is obtained wherein R represents an aminocarbonyl group, this may be converted by dehydration into a corresponding cyano compound of general formula I or if a compound of general formula I is obtained wherein R contains an imino, amino or alkylamino group, this may be converted by acylation into a corresponding alkanoylimino, alkanoylamino, N-alkanoylalkylamino, alkylsulphonylimino, alkylsulphonylamino or N-alkylsulphonyl-alkylamino compound of general formula I or if a compound of general formula I is obtained wherein $R_5$ and $R_6$ each represent a hydrogen atom, this may be converted by transamidination into a corresponding amidino compound of general formula I.

The subsequent hydrolysis is preferably carried out hydrolytically in an aqueous solvent, e.g. in water, ethanol/water, isopropanol/water, tetrahydrofuran/water or dioxane/water, in the presence of an acid such as hydrochloric or sulphuric acid or in the presence of an alkali metal base such as sodium hydroxide or potassium hydroxide at temperatures between 0° and 100° C., but preferably at the boiling temperature of the reaction mixture.

The subsequent dehydration is carried out with a dehydrating agent such as phosphorus pentoxide, phosphorus oxychloride, sulphuric acid or p-toluenesulphonic acid chloride, optionally in a solvent such as methylene chloride or pyridine at temperatures between 0° and 100° C., preferably at temperatures between 20° and 80° C.

The subsequent acylation is conveniently carried out in a solvent or solvent mixture such as water, methylene chloride, chloroform, ether, tetrahydrofuran, dioxane or dimethylformamide with a corresponding carboxylic acid in the presence of an acid-activating or dehydrating agent such as thionyl chloride, with the anhydrides thereof such as acetic anhydride, with the esters thereof such as ethyl acetate, with the halides thereof such as acetyl chloride or methanesulphonyl chloride, optionally in the presence of an inorganic or tertiary organic base, such as sodium hydroxide, potassium carbonate, triethylamine or pyridine, whilst the latter two may simultaneously serve as solvents, at temperatures between −25° and 100° C., but preferably at temperatures between −10° and 80° C.

The subsequent transamidination is preferably carried out in a solvent such as dimethylformamide, dimethylacetamide or dimethylformamide/water and conveniently in the presence of a tertiary organic base such as triethylamine or pyridine in the presence of an amidine such as 3,5-dimethylpyrazole-1-carboxylic acid amidine at temperatures between 0° and 50° C., preferably at ambient temperature.

Moreover, the compounds of general formula I obtained according to the invention may be resolved into the enantiomers thereof and, if the group R contains at least one further chiral centre, into the diastereomers thereof using known methods, e.g. by column chromatography on a chiral phase or by crystallisation with optically active acids such as D- or L-monomethyl tartaric acid, D- or L-diacetyl tartaric acid, D- or L-tartaric acid, D- or L-lactic acid or D- or L-camphoric acid.

Moreover, the compounds of formula I obtained may be converted into the acid addition salts thereof, more particularly for pharmaceutical use the physiologically acceptable salts thereof, with organic or inorganic acids. Suitable acids for this purpose include hydrochloric, hydrobromic, sulphuric, phosphoric, fumaric, succinic, lactic, citric, tartaric and maleic acid.

Moreover, the new compounds of formula I thus obtained, if they contain a carboxy group, may then be converted, if desired, into the addition salts thereof with organic or inorganic bases, more particularly for pharmaceutical use the physiologically acceptable addition salts thereof. Suitable bases include for example sodium hydroxide, potassium hydroxide, cyclohexylamine, ethanolamine, diethanolamine and triethanolamine.

The compounds of general formulae II to V used as starting materials are known from the literature or may be prepared by methods known per se.

A starting compound of formula II is obtained by reacting a corresponding hydroxyalkyl-paracyclophane with a halogenating agent and a starting compound of formula V is obtained by amidation of a corresponding hydroxycarbonylalkyl-paracyclophane.

An optically active starting compound of general formula II or V is obtained starting from a corresponding optically active 4-carboxy-paracyclophane (see for example H. Falck et al. in Tetrahedron 26, 511–527 (1970)) by converting the carboxy group into an —A—$Z_1$ or —A—R group by conventional methods, for example by reduction and subsequent halogenation or by oxidation of the resulting alcohol, followed by ester condensation, hydrogenation and conversion into the corresponding amide.

As already mentioned, the new compounds of formula I have valuable properties. The compounds of formula I wherein R represents a group of the formula

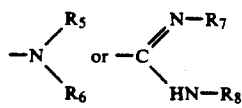

wherein $R_5$ to $R_8$ are as hereinbefore defined, the enantiomers, diastereomers and physiologically acceptable addition salts thereof, have valuable pharmacological properties, more particularly the effect of lowering blood pressure and dilating the coronary blood vessels as well as a mild heart rate lowering activity.

Furthermore, the compounds of formula I wherein R represents a cyano group are valuable intermediate products for preparing the corresponding amino, amidino or guanidino compounds of formula I.

For example, the following compounds:
A=4-(3-(piperidin-1-yl)prop-1-yl)-[2.2]paracyclophane hydrochloride,
B=4-(3-(3-(N-acetyl-methylaminomethyl)piperidin-1-yl)-prop-1-yl)-[2.2]paracyclophane hydrochloride,
C=4-methyl-7-(3-(3-(N-acetyl-methylaminomethyl)-piperidin-1-yl)prop-1-yl)[2.2]paracyclophane oxalate,
D=4-(3-(3-(3-diethylamino-3-oxo-prop-1-yl)piperidin-1-yl)-prop-1-yl)-[2.2]paracyclophane oxalate and
E=4-(2-(piperidin-1-yl)ethoxy-[2.2]paracyclophane oxalate
were investigated for their biological properties as follows:

Effect on Blood Pressure in Rats:

The effect of the test substances on blood pressure was investigated on 2 rats, for each dosage, the rats having an average weight of 350 to 400 g. The rats were anaesthetised with pentobarbital (50 mg/kg i.p.). The test substances were injected in aqueous solution into the Vena femoralis (0.1 ml/100 g).

The blood pressure was measured by means of a cannula inserted into a carotid artery and the heart rate was obtained from the blood pressure signal.

The following Table shows the values found:

| Substance | Dose [mg/kg i.v.] | Maximum reduction in blood pressure in % | Reduction in heart rate in % |
|---|---|---|---|
| A | 1.0 | −27.8 | −10.4 |
| B | 1.0 | −43.1 | −18.0 |
| C | 1.0 | −32.4 | −14.1 |
| D | 1.0 | −48.0 | −17.9 |
| E | 1.0 | −24.2 | −24.8 |

At a dosage of 30 mg/kg i.v. of the above-mentioned compounds A to E, no toxic side effects were observed. The new compounds are therefore well tolerated in therapeutic doses.

In view of their pharmacological properties the new compounds and the physiologically acceptable addition salts thereof are suitable for treating hypertension and for the prevention and treatment of ischaemic heart diseases.

The dosage required to achieve these effects is conveniently, for intravenous administration, 2.5 to 20 mg, preferably 5 to 10 mg, and when administered orally 40 to 120 mg, preferably 60 to 100 mg, once or twice a day. For this purpose the compounds of the formula prepared according to the invention optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water/glycerol, water/sorbitol, water/polyethyleneglycol, propyleneglycol, cetylstearyl alcohol, carboxymethylcellulose or fatty substances such as hard fat or suitable mixtures thereof, in conventional galenic preparations such as plain or coated tablets, capsules, powders, suspensions or suppositories.

The Examples which follow are intended to illustrate the invention:

Preliminary Remarks

The nomenclature and numbering of the cyclophane system in accordance with the system proposed by Vögtle et al. in Tetrahedron 26, 5847 (1970).

EXAMPLE A 4-(3-Hydroxyprop-1-yl)-[2.2]paracyclophane

At 35° C., whilst cooling with ice, 44.86 g (0.16 mol) of 4-(2-carboxyeth-1-yl)-[2.2]paracyclophane, dissolved in 300 ml of absolute tetrahydrofuran, are added dropwise to 9.12 g (0.23 mol) of lithium aluminium hydride in 300 ml of absolute tetrahydrofuran. The mixture is then stirred for 1 hour at ambient temperature, then combined with 9.1 ml of water, 9.1 ml of 15% sodium hydroxide solution and 27 ml of water, whilst cooling with ice. The precipitate is suction filtered, washed with tetrahydrofuran and the filtrate is concentrated by evaporation in vacuo.

Yield: 40.1 g (94% of theory),
Melting point: 78°–80° C.

EXAMPLE B 4-(3-Bromoprop-1-yl)-[2.2]paracyclophane 32.0 g (0.12 mol) of 4-(3-hydroxyprop-1-yl)-[2.2]paracyclophane and 36.7 g (0.14 mol) of triphenylphosphine are dissolved in 650 ml of methylene chloride and cooled to 5° C. Then 46.4 g (0.14 mol) of carbon tetrabromide, dissolved in 70 ml of methylene chloride, are added dropwise whilst cooling with ice water. After stirring for 1 hour at ambient temperature, the reaction mixture is poured into 350 ml of water. The organic phase is separated off, dried over magnesium sulphate and evaporated down in vacuo. The residue is purified by column chromatography over silica gel (particle size: 30 to 60 μm, eluant: cyclohexane).

Yield: 28.3 g (72% of theory),
Melting point: 90°–92° C.

EXAMPLE C 4-(5-(4-Methylpiperazin-1-yl)-5-oxo-pent-1-yl)-[2.2]-paracyclophane 1.23 g (0.004 mol) of 4-(4-carboxybut-1-yl)-[2.2]paracyclophane are dissolved in 20 ml of ethyl acetate, combined with 0.65 g (0.004 mol) of N,N'-carbonyldiimidazole and stirred for 90 minutes at 60° C. 0.44 ml (0.004 mol) of N-methylpiperazine are added to this solution. The resulting mixture is then stirred for one hour at 60° C., then the cooled reaction mixture is extracted twice with 8% sodium hydroxide solution. The organic phase is dried over magnesium sulphate and evaporated down in vacuo.

$R_f$ value: 0.5 (aluminium oxide, neutral; eluant: 3% ethanol in methylene chloride)

EXAMPLE D 4-(5-(2-(Diethylaminomethyl)piperidin-1-yl)-5-oxo-pent-1-yl)-[2.2]paracyclophane 1.23 g (0.004 mol) of 4-(4-carboxybut-1-yl)-[2.2]paracyclophane are dissolved in 30 ml of methylene chloride, combined with 1.2 ml (0.0165 mol) of thionyl chloride and refluxed for 2 hours. After evaporation in vacuo the resulting residue is dissolved in 15 ml of methylene chloride and added dropwise to a solution of 0.68 g (0.004 mol) of 2-(diethylaminomethyl)piperidine and 0.7 ml (0.005 mol) of triethylamine in 20 ml of methylene chloride. The mixture is then stirred for one hour at ambient temperature, then extracted twice with 8% sodium hydroxide solution and once with water. The organic phase is dried over magnesium sulphate and concentrated by evaporation in vacuo.

Yield: 1.80 g (98% of theory),
$R_f$ value: 0.55 (aluminium oxide, neutral; eluant: 3% ethanol in methylene chloride)

EXAMPLE E 4-(3-(N-(3-Methylaminoprop-1-yl)methylamino)prop-1-yl)-[2.2]paracyclophane a)

4-(3-(N-(2-Cyanoeth-1-yl)methylamino)prop-1-yl)-[2.2]paracyclophane

A mixture of 1.40 g (0.005 mol) of 4-(3-methylamino-prop-1-yl)-[2.2]paracyclophane and 0.41 ml (0.00625 mol) of acrylonitrile in 15 ml of methanol is stirred for 3 hours at ambient temperature. The solvent is evaporated down in vacuo and the residue obtained is purified over aluminium oxide (neutral, activity II–III) with methylene chloride/cyclohexane (3/1).

Yield: 1.4 g (84% of theory),
$R_f$ value: 0.4 (silica gel, eluant: 3% ethanol in methylene chloride)

b)

4-(3-(N-(3—Aminoprop-1-yl)methylamino)prop-1-yl)-[2.2]paracyclophane 1.3 g (0.0039 mol) of 4-(3-(N-(2-cyanoeth-1-yl)methylamino)-prop-1-yl)-[2.2]paracyclophane are hydrogenated in 25 ml of methanolic ammonia in the presence of 0.4 g of Raney nickel for 5 hours at 50° C. and under 4 bar of hydrogen. The catalyst is removed by suction filtering and the solvent is distilled off in vacuo.

Yield: 1.28 g (98% of theory),
$R_f$ value: 0.1 (aluminium oxide, eluant: 5% ethanol in methylene chloride)

c)

4-(3-(N-(3-Formylaminoprop-1-yl)methylamino)prop-1-yl)-[2.2]paracyclophane

A mixture of 1.28 g (0.0038 mol) of 4-(3-(N-(3-aminoprop-1-yl)methylamino)prop-1-yl)-[2.2]paracyclophane and 0.17 ml (0.0045 mol) of formic acid in 20 ml of toluene is refluxed for 3 hours using a water separator. The cooled reaction mixture is extracted with 2 molar sodium hydroxide solution. The organic phase is separated off, dried over magnesium sulphate, evaporated down in vacuo and purified over aluminium oxide (neutral, activity II–III) with methylene chloride and subsequently with increasing amounts of ethanol (up to 2%).

Yield: 0.50 g (36% of theory),
$R_f$ value: 0.3 (aluminium oxide, eluant: 3% ethanol in methylene chloride)

d)

4-(3-(N-(3-Methylaminoprop-1-yl)methylamino)prop-1-yl)-[2.2]paracyclophane

Prepared by reduction of 4-(3-(N-(3-formylamino-prop-1-yl)methylamino)prop-1-yl)-[2.2]paracyclophane and lithium aluminium hydride in tetrahydrofuran.

Yield: 97% of theory,
$R_f$ value: 0.15 (aluminium oxide, eluant: 5% ethanol in methylene chloride)

EXAMPLE F 4-(2-Chloroethoxy)-[2.2]paracyclophane 0.9 g (0.004 mol) of 4-hydroxy-[2.2]paracyclophane are dissolved in 40 ml of acetone, mixed with 4.1 g (0.03 mol) of potassium carbonate and stirred for 30 minutes at 40° C. 2.5 ml (0.03 mol) of 1-bromo-2-chloroethane are added dropwise to this suspension. After refluxing for 17 hours, the cooled reaction mixture is filtered and the filtrate is evaporated down in vacuo. The residue is purified by column chromatography over aluminium oxide (neutral, activity II–III) with petroleum ether-/ethyl acetate (10/1).

Yield: 0.75 q (65% of theory),
Melting point: 104°–105° C.

EXAMPLE G 4-(3-Cyanoprop-1-yl)-[2.2]paracyclophane 2.5 g (0.008 mol) of 4-(3-bromoprop-1-yl)-[2.2]paracyclophane are added to a solution of 0.55 g (0.011 mol) of sodium cyanide in 30 ml of dimethylsulphoxide. After stirring for 2 hours at 90° C. the mixture is poured onto ice water. The aqueous solution is extracted 3×with ethyl acetate. The combined organic phases are dried over magnesium sulphate and evaporated down in vacuo. The residue is purified by column chromatography over aluminium oxide (neutral, activity II–III) with methylene chloride/cyclohexane (1/1).

Yield: 1.7 g (81% of theory),
Melting point: 81° C.

EXAMPLE 1

4-(3-(3-(Ethoxycarbonylmethyl)piperidin-1-yl)prop-1-yl)-[2.2]paracyclophane-tartrate A mixture of 0.85 g (0.005 mol) of (piperidin-3-yl)-ethyl acetate, 0.7 ml (0.005 mol) of triethylamine and 1.65 g (0.005 mol) of 4-(3-bromoprop-1-yl)-[2.2]paracyclophane is refluxed for 2 hours. The initial suspension changes into a clear solution and begins to become jelly-like after about 20 minutes. The cooled reaction mixture is dissolved in a mixture of water and ethyl acetate. The organic phase is separated off, washed with water, dried over magnesium sulphate, concentrated by evaporation in vacuo and purified over 150 g of aluminium oxide (neutral, activity II–III) with petroleum ether/ethyl acetate (9/1). The tartrate is precipitated from a solution in acetone/ether with tartaric acid.

Yield: 1.80 g (63% of theory),
Melting point: 68°–70° C. (decomp.)

| Calculated: | C 67.47 | H 7.61 | N 2.46 |
|---|---|---|---|
| Found: | 67.35 | 7.63 | 2.36 |

EXAMPLE 2

4-(5-(2-(Diethylaminomethyl)piperidin-1-yl)pent-1-yl)-[2.2]paracyclophane-dihydrochloride 1.13 g (0.0029 mol) of 4-(5-(2-(diethylaminomethyl)-piperidin-1-yl)-5-oxo-pent-1-yl)-[2.2]paracyclophane, dissolved in 15 ml of absolute tetrahydrofuran, is added dropwise to 0.38 g (0.01 mol) of lithium aluminium hydride in 20 ml of absolute tetrahydrofuran. Then the mixture is stirred for 90 minutes at ambient temperature and subsequently mixed with 0.38 ml of water, 0.38 ml of 15% sodium hydroxide solution and 1.14 ml of water, whilst cooling with ice water. The precipitate is removed by suction filtering, washed with tetrahydrofuran and the filtrate is concentrated by evaporation in vacuo. The dihydrochloride is precipitated from a solution in acetone using methanolic hydrochloric acid.

Yield: 0.80 g (62% of theory),
Melting point: 266°–268° C.

| Calculated: | C 69.47 | H 8.52 | N 6.23 |
|---|---|---|---|
| Found: | 69.42 | 8.54 | 5.98 |

EXAMPLE 3

Sodium salt of 4-(3-(3-(carboxymethyl)piperidin-1-yl)prop-1-yl)-[2.2]paracyclophane 4 ml (0.004 mol) of 1 molar aqueous sodium hydroxide solution are added to 1.53 g (0.00364 mol) of 4-(3-(3-(ethoxycarbonylmethyl)piperidin-1-yl)prop-1-yl)-[2.2]paracyclophane in 5 ml of ethanol. The mixture is then stirred for 5 hours at 80° C., and the sodium salt is subsequently precipitated from the cooled reaction mixture using acetone.

Yield: 1.0 g (66% of theory),
Melting point: 228°–235° C.

| Calculated: | C 75.52 | H 7.80 | N 3.39 |
|---|---|---|---|
| Found: | 75.47 | 7.80 | 3.32 |

EXAMPLE 4

4-(2-Dimethylamino-eth-1-yl)-[2.2]paracyclophanehydrochloride 0.74 g (0.0024 mol) of 4-(2-dimethylamino)-1,2-dioxoeth-1-yl)-[2.2]paracyclophane are added to 10 ml of absolute boron trifluoride etherate and the whole is heated to 60° C. At this temperature, 0.6 ml (0.006 mol) of borane dimethylsulphide complex (10 molar solution) are added dropwise. Then the mixture is refluxed for 5 hours. After the reaction mixture has cooled, methanol is added dropwise thereto, then 10 ml of methanolic hydrochloric acid are added and the resulting mixture is refluxed for a further 3 hours. After the solvent has been evaporated off the mixture is dissolved in acetone and the hydrochloride is precipitated with ether.

Yield: 0.50 g (66% of theory),
Melting point: 194°–196° C.

| Calculated: | C 76.05 | H 8.30 | N 4.43 |
|---|---|---|---|
| Found: | 75.95 | 8.32 | 4.23 |

EXAMPLE 5

4-(3-(3-(2-Cyanoeth-1-yl)piperidin-1-yl)prop-1-yl)-[2.2]paracyclophane-oxalate

A mixture of 0.34 mol (0.00084 mol) of 4-(3-(3-(3-amino-3-oxo-prop-1-yl)piperidin-1-yl)prop-1-yl)-[2.2]paracyclophane and 0.92 g (0.006 mol) of phosphorus oxychloride is heated to 80° C. for 40 minutes. Water is added to the cooled reaction mixture which is then made alkaline with concentrated sodium hydroxide solution. It is then extracted 3 times with ethyl acetate, dried over magnesium sulphate and concentrated by evaporation in vacuo. The oxalate is precipitated from a solution in ethyl acetate using oxalic acid.

Yield: 0.24 g (60% of theory),
Melting point: 200°–201 C

| Calculated: | C 73.08 | H 7.61 | N 5.88 |

| Found: | 72.96 | 7.63 | 5.90 |
|---|---|---|---|

EXAMPLE 6

4-(3-(Piperazin-1-yl)prop-1-yl)-[2.2]paracyclophanedihydrochloride

A mixture of 3.0 g (0.0074 mol) of 4-(3-(4-ethoxycarbonyl-piperazin-1-yl)prop-1-yl)-2.2]paracyclophane, 20 ml of ethanol and 40 ml of 8 molar sodium hydroxide solution is refluxed for 12 hours. After evaporation in vacuo, the residue obtained is extracted twice with ethyl acetate, dried over magnesium sulphate and concentrated by evaporation in vacuo. The dihydrochloride is precipitated from a solution in acetone using methanolic hydrochloric acid.

Yield: 2.37 g (80% of theory),
Melting point: 274°-278° C.

| Calculated: | C 67.80 | H 7.92 | N 6.88 |
|---|---|---|---|
| Found: | 67.66 | 8.06 | 6.81 |

EXAMPLE 7

4-(3-(4—Acetyl-piperazin-1-yl)prop-1-yl)-[2.2]paracyclophane-hydrochloride 0.67 g (0.002 mol) of 4-(3-(piperazin-1-yl)-[2.2]paracyclophane and 0.30 ml (0.002 mol) of triethylamine are dissolved in 15 ml of methylene chloride and 0.16 ml (0.0022 mol) of acetyl chloride are added dropwise with stirring. After 30 minutes, water is added. The aqueous phase is extracted twice with methylene chloride. The organic phase is dried over magnesium sulphate and concentrated by evaporation in vacuo. The residue is dissolved in acetone and the hydrochloride is precipitated from it using methanolic hydrochloric acid.

Yield: 0.56 g (68% of theory),
Melting point: 153°-158° C. (decomp.)

| Calculated: | C 72.70 | H 8.05 | N 6.78 |
|---|---|---|---|
| Found: | 72.56 | 8.31 | 6.62 |

EXAMPLE 8

4-(3-Guanidinoprop-1-yl)-[2.2]paracyclophanehydrochloride

To a solution of 2.3 g (0.012 mol) of 3,5-dimethylpyrazole-1-carboxylic acid amidine in 15 ml of dimethylformamide/water (2/1) are added 0.7 g (0.002 mol) of 4-(3-aminoprop-1-yl)-[2.2]paracyclophane-hydrochloride and 0.5 g (0.005 mol) of triethylamine. The solution is left to stand at ambient temperature for 5 days and the solvent is then evaporated off in vacuo. The residue is purified by column chromatography over silica gel (particle size: 30–60 μm, eluant: methylene chloride containing 10% ethanol).

Yield: 0.21 g (27% of theory),
Melting point: 139° C.

| Calculated: | C 61.50 | H 7.16 | N 12.05 | Cl 14.32 |
|---|---|---|---|---|
| Found: | 61.47 | 7.17 | 11.83 | 13.96 |

EXAMPLE 9

4-(3-(N,N'-Dimethylamidino)prop-1-yl)-[2.2]paracyclophane-hydrochloride 0.5 g (0.002 mol) of 4-(3-cyanoprop-1-yl)-[2.2]paracyclophane are dissolved in 10 ml of absolute methanol and 20 ml of absolute diethylether under nitrogen. At −5° C. hydrogen chloride gas is bubbled in for 30 minutes and the solution is stirred for a further hour at ambient temperature. Then the solvent is evaporated off to leave no residue. The resulting oil is dissolved in 20 ml of absolute methanol and carefully added dropwise at 0° C. to a saturated solution of methylamine in 35 ml of absolute diethylether. The mixture is stirred for 20 hours at ambient temperature and then concentrated by evaporation in vacuo. The residue is triturated with diethylether and the precipitate formed is suction filtered and dried.

Yield: 0.41 g (64% of theory),
Melting point: 192° C.

| Calculated: | C 73.25 | H 8.23 | N 7.62 |
|---|---|---|---|
| Found: | 73.03 | 8.19 | 7.85 |

EXAMPLE 10

4-(2-(Piperidin-1-yl)ethoxy-[2.2]paracyclopane-oxalate

Prepared analogously to Example 1 from 4-(2-chloroethoxy)-[2.2]paracyclophane and piperidine.

Yield: 16% of theory,
Melting point: 186° C.

| Calculated: | C 70.57 | H 7.34 | N 3.29 |
|---|---|---|---|
| Found: | 70.43 | 7.35 | 3.43 |

EXAMPLE 11

4-(3-(Adamantyl-1-amino)prop-1-yl)-[2.2]paracyclophanehydrochloride

Prepared analogously to Example 1 from 4-(3-bromoprop-1-yl)-[2.2]paracyclophane and 1-adamantylamine.

Yield: 31% of theory,
Melting point: 285° C.

| Calculated: | C 79.87 | H 8.78 | N 3.21 | Cl 8.13 |
|---|---|---|---|---|
| Found: | 79.67 | 8.99 | 2.93 | 8.33 |

EXAMPLE 12

4-(3-(3,5-Dimethyladamantyl-1-amino)prop-1-yl)-[2.2]-paracyclophane-hydrochloride Prepared analogously to Example 1 from 4-(3-bromoprop-1-yl)-[2.2]paracyclophane and 3,5-dimethyl-1-adamantylamine.

Yield: 19% of theory,
Melting Point: 301° C.

| Calculated: | C 80.22 | H 9.12 | N 3.02 | Cl 7.64 |
|---|---|---|---|---|
| Found: | 79.94 | 9.25 | 2.86 | 7.57 |

EXAMPLE 13

4-(3-(Piperidin-1-yl)propoxy)-[2.2]paracyclophanehydrochloride

Prepared analogously to Example 1 from 4-(3-bromopropoxy)-[2.2]paracyclophane and piperidine.
Yield: 46% of theory,
Melting point: 179° C.

| Calculated: | C 74.68 | H 8.36 | N 3.63 | Cl 9.18 |
|---|---|---|---|---|
| Found: | 74.59 | 8.32 | 3.56 | 9.37 |

EXAMPLE 14

-(3-(3-(2-Dimethylamino-2-oxo-eth-1-yl)piperidin-1-yl)propoxy)-[2.2]paracyclophane-oxalate Prepared analogously to Example 1 from 4-(3-bromopropoxy)-[ 2.2]paracyclophane and (piperidin-3-yl)acetic acid dimethylamide.
Yield: 34% of theory,
Melting point: 169° C.

| Calculated: | C 68.68 | H 7.69 | N 5.34 |
|---|---|---|---|
| Found: | 68.71 | 7.77 | 5.13 |

EXAMPLE 15

4-(3-(3-(2-Dimethylamino-2-oxo-eth-1-yl)piperidin-1-yl)prop-1-yl)-[2.2]paracyclophane-oxalate Prepared analogously to Example 1 from 4-(3-bromoprop-1-yl)-[2.2]paracyclophane and (piperidin-3-yl)-acetic acid dimethylamide.
Yield: 41% of theory,
Melting point: >85° C. (decomp.)

| Calculated: | C 70.84 | H 7.93 | N 5.51 |
|---|---|---|---|
| Found: | 71.02 | 8.16 | 5.38 |

EXAMPLE 16

4-(3-(3-(2-Ethoxycarbonyl-eth-1-yl)piperidin-1-yl)prop-1-yl)-[2.2]paracyclophane-oxalate Prepared analogously to Example 1 from 4-(3-bromoprop-1-yl)-[2.2]paracyclophane and 3-(piperidin-3-yl)propionate.
Yield: 70% of theory,
Melting point: 175° C.

| Calculated: | C 71.10 | H 7.89 | N 2.67 |
|---|---|---|---|
| Found: | 71.11 | 8.06 | 2.72 |

EXAMPLE 17

-(3-(3-(Hydroxycarbonyl)piperidin-1-yl)prop-1-yl)-[ 2.2]paracyclophane

Prepared analogously to Example 3 from 4-(3-(3-(ethoxycarbonyl)-piperidin-1-yl)prop-1-yl)-[2.2]paracyclophane and sodium hydroxide solution.
Yield: 42% of theory,
Melting point: 128° C.

| Calculated: | C 79.54 | H 8.28 | N 3.71 |
|---|---|---|---|
| Found: | 76.95 | 8.38 | 3.68 |

EXAMPLE 18

4-(3-(4—Acetyl-1,4-diazacyclohept-1-yl)prop-1-yl)-[2.2]paracyclophane-oxalate Prepared analogously to Example 7 from 4-(3-(1,4-diazacyclohept-1-yl)prop-1-yl)-[2.2]paracyclophane and acetyl chloride.
Yield: 40% of theory
Melting point: 151° C.

| Calculated: | C 69.98 | H 7.55 | N 5.83 |
|---|---|---|---|
| Found: | 69.81 | 7.46 | 5.66 |

EXAMPLE 19

4-(3-tert.Butylamino-prop-1-yl)-[2.2]paracyclophanehydrochloride

Prepared analogously to Example 1 from 4-(3-bromoprop-1-yl)-[2.2]paracyclophane and tert.butylamine.
Yield: 64% of theory,
Melting point: 251° C.

| Calculated: | C 77.17 | H 9.01 | N 3.91 | Cl 9.90 |
|---|---|---|---|---|
| Found: | 77.17 | 9.14 | 3.89 | 9.69 |

EXAMPLE 20

4-(3-(3-(2-Hydroxyeth-1-yl)piperidin-1-yl)prop-1-yl)-[2.2]paracyclophane-hydrochloride Prepared analogously to Example 2 from 4-(3-(3-(ethoxycarbonylmethyl)piperidin-1-yl)prop-1-yl)-[2.2]paracyclophane and lithium aluminium hydride.
Yield: 75% of theory,
Melting point: 191° C.

| Calculated: | C 75.42 | H 8.76 | N 3.38 | Cl 8.56 |
|---|---|---|---|---|
| Found: | 75.32 | 8.93 | 3.20 | 8.73 |

EXAMPLE 21

4-(3-(3-(N-Methanesulphonyl-methylamino-methyl)-piperidin-1-yl)-prop-1-yl)-[2.2]paracyclophane-fumarate Prepared analogously to Example 7 from 4-(3-(3-(methylamino-methyl)piperidin-1-yl)prop-1-yl)-[2.2]paracyclophane and methanesulphonic acid chloride.
Yield: 50% of theory,
Melting point: 110° C. (decomp.)

| Calculated: | C 65.24 | H 7.42 | N 4.91 | Cl 5.62 |
|---|---|---|---|---|
| Found: | 65.30 | 7.62 | 4.82 | 5.47 |

EXAMPLE 22

4-(3-(N-(n-Octyl)methylamino)prop-1-yl)-[2.2]paracyclophane-oxalate

Prepared analogously to Example 2 from 4-(3-(N-(n-octyl)methylamino)-3-oxo-prop-1-yl)-[2.2]paracyclophane and lithium aluminium hydride.
Yield: 56% of theory,
Melting point: 141° C.

| Calculated: | C 74.81 | H 9.00 | N 2.91 |
| --- | --- | --- | --- |
| Found: | 74.79 | 8.89 | 2.89 |

EXAMPLE 23

4-(3-(N-(2-Cyclohexyl-eth-1-yl)methylamino)prop-1-yl)-[2.2]paracyclophane-oxalate Prepared analogously to Example 1 from 4-(3-methylaminoprop-1-yl)-[2.2]paracyclophane and 1-bromo-2-cyclohexylethane.
Yield: 36% of theory, Melting point: 134° C.

| Calculated: | C 75.12 | H 8.62 | N 2.92 |
| --- | --- | --- | --- |
| Found: | 74.98 | 8.59 | 2.81 |

EXAMPLE 24

4-(3-(4-(Ethoxycarbonyl)piperazin-1-yl)prop-1-yl)-[2.2]paracyclophane-hydrochloride Prepared analogously to Example 1 from 4-(3-bromo-prop-1-yl)-[2,2]paracyclophane and N-ethoxycarbonyl-piperazine.
Yield: 70% of theory,
Melting point: 229° C. (decomp.)

| Calculated: | C 70.49 | H 7.96 | N 6.32 | Cl 8.00 |
| --- | --- | --- | --- | --- |
| Found: | 70.55 | 8.06 | 6.47 | 8.18 |

EXAMPLE 25

-(3-(3-(N-Acetyl-aminomethyl)piperidin-1-yl)prop-1-yl)-[ 2.2]paracyclophane-hydrochloride Prepared analogously to Example 1 from 4-(3-bromo-prop-1-yl)-[2.2]paracyclophane and 3-(N-acetyl-aminomethyl)piperidine.
Yield: 37% of theory,
Melting point: 125° C. (decomp.)

| Calculated: | C 73.53 | H 8.46 | N 6.35 | Cl 8.04 |
| --- | --- | --- | --- | --- |
| Found: | 73.40 | 8.51 | 6.28 | 8.22 |

EXAMPLE 26

4-(3-(3-(N-Acetyl-methylamino-methyl)piperidin-1-yl)prop-1-yl)-[2.2]paracyclophane-hydrochloride Prepared analogously to Example 1 from 4-(3-bromo-prop-1-yl)-[2.2]paracyclophane and 3-(N-acetyl-methylaminomethyl)piperidine.
Yield: 30% of theory,
Melting point: 105° C.

| Calculated: | C 73.90 | H 8.64 | N 6.16 | Cl 7.79 |
| --- | --- | --- | --- | --- |
| Found: | 73.70 | 8.73 | 6.02 | 7.85 |

EXAMPLE 27

4-(3-(3-(Hydroxymethyl)piperidin-1-yl)prop-1-yl)-[2.2]paracyclophane-hydrochloride Prepared analogously to Example 1 from 4-(3-bromo-prop-1-yl)-[2.2]paracyclophane and 3-hydroxymethyl-piperidine.
Yield: 50% of theory,
Melting point: 187° C.

| Calculated: | C 75.07 | H 8.57 | N 3.50 | Cl 8.86 |
| --- | --- | --- | --- | --- |
| Found: | 74.93 | 8.65 | 3.44 | 9.02 |

EXAMPLE 28

4-(3-(Acetoxymethyl)piperidin-1-yl)prop-1-yl)-[2.2]paracyclophane-tartrate

Prepared analogously to Example 7 from 4-(3-(3-(hydroxymethyl)piperidin-1-yl)prop-1-yl)-[2.2]paracyclophane and acetylchloride.
Yield: 70% of theory,
Melting point: 65-70° C. (decomp.)

| Calculated: | C 67.01 | H 7.44 | N 2.52 |
| --- | --- | --- | --- |
| Found: | 66.80 | 7.56 | 2.34 |

EXAMPLE 29

4-(3-(3-(Ethoxycarbonyl)piperidin-1-yl)prop-1-yl)-[2.2]paracyclophane-tartrate

Prepared analogously to Example 1 from 4-(3-bromo-prop-1-yl)paracyclophane and ethyl-(piperidin-3-yl)carboxylate.
Yield: 35% of theory,
Melting point: 90-91° C. (decomp.)

| Calculated: | C 67.01 | H 7.44 | N 2.52 |
| --- | --- | --- | --- |
| Found: | 66.81 | 7.53 | 2.49 |

EXAMPLE 30

4-(3-(4-(Ethoxycarbonyl)piperidin-1-yl)prop-1-yl)-[2.2]paracyclophane-tartrate

Prepared analogously to Example 1 from 4-(3-bromo-prop-1 -yl)-[2.2]paracyclophane and ethyl-(piperidin-4-yl)carboxylate.
Yield: 30% of theory,
Melting point: >60° C. (decomp.)

| Calculated: | C 67.01 | H 7.44 | N 2.52 |
| --- | --- | --- | --- |
| Found: | 66.84 | 7.32 | 2.35 |

EXAMPLE 31

4-(3-[N-(2-(3,4-Dimethoxyphenyl)eth-1-yl)methylamino]-prop-1-yl)-[2.2]paracyclophane-hydrochloride Prepared analogously to Example 1 from 4-(3-bromoprop-1-yl)-[2.2]paracyclophane and N-methylhomoveratrylamine.
Yield: 30% of theory,
Melting point: 146° C.

| Calculated: | C 75.05 | H 7.98 | N 2.92 | Cl 7.39 |
|---|---|---|---|---|
| Found: | 74.95 | 8.10 | 2.83 | 7.14 |

EXAMPLE 32

4-(4-(2-(Diethylaminomethyl)piperidin-1-yl)but-1-yl)-[2.2]paracyclophane-dihydrochloride Prepared analogously to Example 2 from 4-(4-(2-(diethylaminomethyl)piperidin-1-yl)-4-oxo-but-1-yl)-[2.2]paracyclophane and lithium aluminium hydride.
Yield: 41% of theory,
Melting point: >100° C. (decomp.)

| Calculated: | C 71.26 | H 9.17 | N 5.54 | Cl 14.03 |
|---|---|---|---|---|
| Found: | 70.97 | 9.28 | 5.36 | 13.96 |

EXAMPLE 33

4-(4-(4-Methylpiperazin-1-yl)but-1-yl)-[2.2]-paracyclophane-dihydrochloride

Prepared analogously to Example 2 from 4-(4-(4-(methylpiperazin-1-yl)-4-oxo-but-1-yl)-[2.2]paracyclophane and lithium aluminium hydride.
Yield: 66% of theory,
Melting point: 282° C.

| Calculated: | C 68.95 | H 8.33 | N 6.43 | Cl 16.28 |
|---|---|---|---|---|
| Found: | 68.86 | 8.25 | 6.57 | 16.35 |

EXAMPLE 34

4-(3-(Piperidin-1-yl)prop-1-yl)-[2.2]-paracyclophanehydrochloride

Prepared analogously to Example 2 from 4-(3-(piperidin-1-yl)-3-oxo-prop-1-yl)-[2.2]paracyclophane and lithium aluminium hydride.
Yield: 55% of theory,
Melting point: 244° C.

| Calculated: | C 77.91 | H 8.72 | N 3.79 | Cl 9.58 |
|---|---|---|---|---|
| Found: | 77.80 | 8.59 | 3.86 | 9.33 |

EXAMPLE 35

4-(3-(4-(2-(4-Trifluoromethylphenoxy)eth-1-yl)piperazin-1-yl)-prop-1-yl)-[2.2]paracyclophane-dihydrochloride Prepared analogously to Example 1 from 4-(3-(piperazin-1-yl)prop-1-yl)-[2.2]paracyclophane and 1-bromo-2-(4-trifluoromethylphenoxy)ethane.
Yield: 30% of theory,
Melting point: 241° C.

| Calculated: | C 64.53 | H 6.60 | N 4.70 | Cl 11.91 |
|---|---|---|---|---|
| Found: | 64.64 | 6.69 | 4.54 | 11.79 |

EXAMPLE 36

4-(3-(4-(2-(4-Fluorophenoxy)eth-1-yl)piperazin-1-yl)-prop-1-yl)-[2.2]paracyclophane-dihydrochloride Prepared analogously to Example 1 from 4-(3-(piperazin-1-yl)prop-1-yl)-[2.2]paracyclophane and 1-bromo-2-(4-fluorophenoxy)ethane.
Yield: 41% of theory,
Melting point: 254° C.

| Calculated: | C 68.25 | H 7.21 | N 5.14 | Cl 13.00 |
|---|---|---|---|---|
| Found: | 68.40 | 7.17 | 5.20 | 13.05 |

EXAMPLE 37

4-(3-(4-(2-(4-Nitrophenoxy)eth-1-yl)piperazin-1-yl)prop-1-yl)-[2.2]paracyclophane-dihydrochloride Prepared analogously to Example 1 from 4-(3-(bromoprop-1-yl)-[2.2]paracyclophane and 1-(2-(4-nitrophenoxy)eth-1-yl)piperazine.
Yield: 48% of theory,
Melting point: 241° C.

| Calculated: | C 65.03 | H 6.87 | N 7.34 | Cl 12.38 |
|---|---|---|---|---|
| Found: | 65.00 | 6.95 | 7.24 | 12.30 |

EXAMPLE 38

4-(5-(4-Methylpiperazin-1-yl)pent-1-yl)-[2.2]paracyclophane-dihydrochloride

Prepared analogously to Example 2 from 4-(5-(4-methylpiperazin-1-yl)-5-oxo-pent-1-yl)-[2.2]paracyclophane and lithium aluminium hydride.
Yield: 62% of theory,
Melting point: 267° C.

| Calculated: | C 69.47 | H 8.52 | N 6.23 | Cl 15.78 |
|---|---|---|---|---|
| Found: | 69.42 | 8.54 | 6.10 | 16.00 |

EXAMPLE 39

4-(3-(4-Methylpiperazin-1-yl)prop-1-en-1-yl)-[2.2]paracyclophane-dihydrochloride Prepared analogously to Example 2 from 4-(3-(4-methylpiperazin-1-yl)-3-oxo-prop-1-en-1-yl)-[2.2]paracyclophane and lithium aluminium hydride.
Yield: 63% of theory,
Melting point: 239° C.

| Calculated: | C 68.72 | H 7.69 | N 6.68 | Cl 16.91 |
|---|---|---|---|---|
| Found: | 68.59 | 7.80 | 6.45 | 16.86 |

EXAMPLE 40

4-(3-(2-(Diethylaminomethyl)piperidin-1-yl)prop-1-yl)-[2.2]paracyclophane-dihydrochloride Prepared analogously to Example 2 from 4-(3-(2-(diethylaminomethyl)piperidin-1-yl)-3-oxo-prop-1-yl)-[2,2]paracyclophane and lithium aluminium hydride.
Yield: 43% of theory,
Melting point: 149°-151° C.

| | | | | | | | |
|---|---|---|---|---|---|---|---|
| Calculated: | C | 70.85 | H | 9.02 | N | 5.70 | Cl 14.43 |
| Found: | | 70.37 | | 8.91 | | 5.65 | 14.30 |

EXAMPLE 41

4-(3-(4-(3-Phenylprop-2-en-1-yl)piperazin-1-yl)prop-1-yl)-[2.2]paracyclophane-dihydrochloride Prepared analogously to Example 2 from 4-(3-(4-(3-phenylprop-2-en-1-yl)piperazin-1-yl)-3-oxo-prop-1-yl)-[2,2]paracyclophane and lithium aluminium hydride.
Yield: 49% of theory,
Melting point: 253°-255° C.

| | | | | | | | |
|---|---|---|---|---|---|---|---|
| Calculated: | C | 73.41 | H | 7.70 | N | 5.35 | Cl 13.54 |
| Found: | | 73.22 | | 7.79 | | 5.67 | 13.32 |

EXAMPLE 42

4-(3-(4-Methylpiperazin-1-yl)prop-1-yl)-[2.2]paracyclophane-dihydrochloride

Prepared analogously to Example 2 from 4-(3-(4-methylpiperazin-1-yl)-3-oxo-prop-1-yl)-[2.2]paracyclophane and lithium aluminium hydride.
Yield: 76% of theory,
Melting point: 262°-263° C.

| | | | | | | | |
|---|---|---|---|---|---|---|---|
| Calculated: | C | 68.39 | H | 8.13 | N | 6.65 | Cl 16.83 |
| Found: | | 68.27 | | 8.23 | | 6.61 | 16.61 |

EXAMPLE 43

4-(3-Dimethylamino-prop-1-yl)-[2.2]paracyclophane-dihydrochloride

Prepared Analogously to Example 2 from 4-(3-dimethylamino-3-oxo-prop-1-yl)-[2.2]paracyclophane and lithium aluminium hydride.
Yield: 72% of theory,
Melting point: 99°-101° C.

| | | | | | | | |
|---|---|---|---|---|---|---|---|
| Calculated: | C | 76.45 | H | 8.55 | N | 4.25 | Cl 10.75 |
| Found: | | 76.35 | | 8.67 | | 4.19 | 10.76 |

EXAMPLE 44

4-(3-Methylamino-prop-1-yl)-[2.2]paracyclophane-hydrochloride

Prepared analogously to Example 2 from 4-(3-methylamino-3-oxo-prop-1-yl)-[2.2]paracyclophane and lithium aluminium hydride.
Yield: 62% of theory,
Melting point: 215°-218° C.

| | | | | | | | |
|---|---|---|---|---|---|---|---|
| Calculated: | C | 76.05 | H | 8.30 | N | 4.43 | Cl 11.22 |
| Found: | | 75.95 | | 8.55 | | 4.17 | 11.19 |

EXAMPLE 45

4-(2-(4-Benzylpiperazin-1-yl)eth-1-yl)-[2.2]paracyclophane-dihydrochloride

Prepared analogously to Example 2 from 4-(2-(4-benzylpiperazin-1-yl)-2-oxo-eth-1-yl)-[2.2]paracyclophane and lithium aluminium hydride.
Yield: 80% of theory,
Melting point: 245°-248° C.

| | | | | | | | |
|---|---|---|---|---|---|---|---|
| Calculated: | C | 72.04 | H | 7.50 | N | 5.79 | Cl 14.67 |
| Found: | | 72.14 | | 7.59 | | 5.88 | 14.60 |

EXAMPLE 46

4-(2-(4-(3-Phenyl-prop-2-en-1-yl)piperazin-1-yl)eth-1-yl)-[2.2]paracyclophane-dihydrochloride Prepared analogously to Example 2 from 4-(2-(4-(3-phenyl-1-oxo-prop-2-en-1-yl)piperazin-1-yl)eth-1-yl)-[2.2]paracyclophane and lithium aluminium hydride.
Yield: 40% of theory,
Melting point: 252°-254° C.

| | | | | | | | |
|---|---|---|---|---|---|---|---|
| Calculated: | C | 73.07 | H | 7.52 | N | 5.50 | Cl 13.91 |
| Found: | | 72.90 | | 7.62 | | 5.34 | 13.71 |

EXAMPLE 47

4-(2-(4-Methylpiperazin-1-yl)eth-1-yl)-[2.2]paracyclophane-dihydrochloride

Prepared analogously to Example 2 from 4-(2-(4-methylpiperazin-1-yl)-2-oxo-eth-1-yl)-[2.2]paracyclophane and lithium aluminium hydride.
Yield: 69% of theory,
Melting point: 268°-270° C.

| | | | | | | | |
|---|---|---|---|---|---|---|---|
| Calculated: | C | 67.80 | H | 7.92 | N | 6.88 | Cl 17.40 |
| Found: | | 67.93 | | 7.81 | | 6.94 | 17.65 |

EXAMPLE 48

4-(2-(N-Morpholino)eth-1-yl)-[2.2]paracyclophane-dihydrochloride

Prepared analogously to Example 2 from 4-(2-(N-morpholino)-2-oxo-eth-1-yl)-[2.2]paracyclophane and lithium aluminium hydride.
Yield: 63% of theory,
Melting point: 105°-107° C.

| | | | | | | |
|---|---|---|---|---|---|---|
| Calculated: | C | 82.20 | H | 8.47 | N | 4.36 | |
| Found: | | 82.18 | | 8.50 | | 4.26 | |

EXAMPLE 49

4-(2-(Piperidin-1-yl)eth-1-yl)-[2.2]paracyclophane-hydrochloride

Prepared analogously to Example 2 from 4-(2-(piperidin-1-yl)-2-oxo-eth-1-yl)-[2.2]paracyclophane and lithium aluminium hydride.

Yield: 60% of theory,
Melting point: 249°–252° C.

| | | | | |
|---|---|---|---|---|
| Calculated: | C 77.61 | H 8.50 | N 3.94 | Cl 9.96 |
| Found: | 77.60 | 8.58 | 3.76 | 10.10 |

EXAMPLE 50

4-(2-(Pyrrolidin-1-yl)eth-1-yl)-[2.2]paracyclophane-hydrochloride

Prepared analogously to Example 2 from 4-(2-(pyrrolidin-1-yl)-2-oxo-eth-1-yl)-[2.2]paracyclophane and lithium aluminium hydride.

Yield: 63% of theory,
Melting point: 231°–233° C.

| | | | | |
|---|---|---|---|---|
| Calculated: | C 77.28 | H 8.25 | N 4.10 | Cl 10.37 |
| Found: | 77.16 | 8.32 | 3.99 | 10.23 |

EXAMPLE 51

4-(2-(Di-n-propylamino)eth-1-yl)-[2.2]paracyclophane-hydrochloride

Prepared analogously to Example 2 from 4-(2-(di-n-propylamino)-2-oxo-eth-1-yl)-[2.2]paracyclophane and lithium aluminium hydride.

Yield: 54% of theory,
Melting point: 168°–169° C.

| | | | | |
|---|---|---|---|---|
| Calculated: | C 77.49 | H 9.21 | N 3.77 | Cl 9.53 |
| Found: | 77.31 | 9.28 | 3.63 | 9.71 |

EXAMPLE 52

4-Dimethylaminomethyl-[2.2]paracyclophane-hydrochloride

Prepared analogously to Example 2 from 4-dimethylamino-carbonyl-[2.2]paracyclophane and lithium aluminium hydride.

Yield: 60% of theory,
Melting point: 242°–243° C.

| | | | | |
|---|---|---|---|---|
| Calculated: | C 75.60 | H 8.01 | N 4.64 | Cl 11.75 |
| Found: | 75.49 | 7.99 | 4.45 | 11.50 |

EXAMPLE 53

4-Methylaminomethyl-[2.2]paracyclophane-hydrochloride

Prepared analogously to Example 2 from 4-methylaminocarbonyl-[2.2]paracyclophane and lithium aluminium hydride.

Yield: 70% of theory,
Melting point: 249°–250° C.

| | | | | |
|---|---|---|---|---|
| Calculated: | C 75.11 | H 7.70 | N 4.87 | Cl 12.32 |
| Found: | 74.97 | 7.56 | 4.72 | 12.04 |

EXAMPLE 54

4-(2-Diethylamino-eth-1-yl)-[2.2]paracyclophane-hydrochloride

Prepared analogously to Example 2 from 4-(2-diethylamino-2-oxo-eth-1-yl)-[2.2]paracyclophane and lithium aluminium hydride.

Yield: 37% of theory,
Melting point: 215°–217° C.

| | | | | |
|---|---|---|---|---|
| Calculated: | C 76.83 | H 8.79 | N 4.07 | Cl 10.31 |
| Found: | 76.72 | 8.75 | 4.06 | 10.26 |

EXAMPLE 55

4-(2-Methylamino-eth-1-yl)-[2.2]paracyclophane-hydrochloride

Prepared analogously to Example 4 from 4-(2-(methylamino)-1,2-dioxo-eth-1-yl)-[2.2]paracyclophane and borane/dimethylsulphide complex (10 molar solution).

Yield: 63% of theory,
Melting point: 280°–281° C.

| | | | | |
|---|---|---|---|---|
| Calculated: | C 75.60 | H 8.01 | N 4.64 | Cl 11.75 |
| Found: | 75.40 | 7.95 | 4.42 | 11.57 |

EXAMPLE 56

4-(2-Aminoeth-1-yl)-[2.2]paracyclophane-hydrochloride

Prepared analogously to Example 4 from 4-(2-amino-1,2-dioxo-eth-1-yl)-[2.2]paracyclophane and borane dimethylsulphide complex (10 molar solution).

Yield: 40% of theory,
Melting point: 150°–152° C.

| | | | | |
|---|---|---|---|---|
| Calculated: | C 75.11 | H 7.70 | N 4.87 | Cl 12.32 |
| Found: | 75.06 | 8.06 | 4.84 | 12.12 |

EXAMPLE 57

4-(2-tert.Butylamino-eth-1-yl)-[2.2]paracyclophane-hydrochloride

Prepared analogously to Example 4 from 4-(2-tert.butylamino-1,2-dioxo-eth-1-yl)-[2.2]paracyclophane and borane dimethylsulphide complex (10 molar solution).

Yield: 40% of theory,
Melting point: 276°–279° C.

| | | | | |
|---|---|---|---|---|
| Calculated: | C 76.83 | H 8.79 | N 4.07 | Cl 10.31 |
| Found: | 76.66 | 8.95 | 3.93 | 10.18 |

EXAMPLE 58

4-(3-(4-(2-(3,4,5-Trimethoxyphenyl)eth-1-yl)piperazin-1-yl)-prop-1-yl)-[2.2]paracyclophane-dihydrochloride Prepared analogously to Example 1 from 4-(3-bromoprop-1-yl)-[2.2]paracyclophane and 1-(2-(3,4,5-trimethoxyphenyl)eth-1-yl)piperazine.
Yield: 51% of theory,
Melting point: 260°-262° C.

| Calculated: | C 67.87 | H 7.71 | N 4.66 | Cl 11.79 |
|---|---|---|---|---|
| Found: | 67.66 | 7.74 | 4.51 | 11.81 |

EXAMPLE 59

4-(3-(4-(2-(p-Tolyloxy)eth-1-yl)-piperazin-1-yl)prop-1-yl)-[2.2]paracyclophane-dihydrochloride Prepared analogously to Example 1 from 4-(3-bromoprop-1-yl)-[2.2]paracyclophane and 1-(2-(p-tolyloxy)eth-1-yl)piperazine.
Yield: 52% of theory,
Melting point: 258°-260° C.

| Calculated: | C 70.96 | H 7.82 | N 5.17 | Cl 13.09 |
|---|---|---|---|---|
| Found: | 70.83 | 8.05 | 5.09 | 12.85 |

EXAMPLE 60

4-(3-(3-Piperidin-1-yl)prop-1-yn-1-yl)-[2.2]paracyclophane-dioxalate

Prepared analogously to Example 1 from 4-(3-chloroprop-1-yn-yl)-[2.2]paracyclophane and piperidine.
Yield: 38% of theory,
Melting point: 150°-151° C.

| Calculated: | C 66.00 | H 6.13 | N 2.75 |
|---|---|---|---|
| Found: | 67.89 | 6.27 | 3.09 |

EXAMPLE 61

4-(3-(4-(3-Dimethylamino-3-oxo-prop-1-yl)piperidin-1-yl)-prop-1-yl)-[2.2]paracyclophane-oxalate Prepared analogously to Example 1 from 4-(3-bromoprop-1-yl)-[2.2]paracyclophane and 3-(piperidin-4-yl)propionic acid dimethylamide.
Yield: 20% of theory,
Melting point: 175° C. (decomp.)

| Calculated: | C 71.24 | H 8.10 | N 5.36 |
|---|---|---|---|
| Found: | 71.15 | 8.24 | 5.31 |

EXAMPLE 62

4-(3-(4-(3-Dimethylamino-4-oxo-but-1-yl)piperidin-1-yl)prop-1-yl)-[2.2]paracyclophane-oxalate Prepared analogously to Example 1 from 4-(3-bromoprop-1-yl)-[2.2]paracyclophane and 3-(piperidin-4-yl)-butyric acid dimethylamide.
Yield: 46% of theory,
Melting point: 185° C.

| Calculated: | C 71.61 | H 8.26 | N 5.22 |
|---|---|---|---|
| Found: | 71.40 | 8.20 | 5.14 |

EXAMPLE 63

4-(3-(4-(2-Dimethylamino-2-oxo-eth-1-yl)piperidin-1-yl)-prop-1-yl)-[2.2]paracyclophane-oxalate Prepared analogously to Example 1 from 4-(3-bromoprop-1-yl)-[2.2]paracyclophane and (piperidin-4-yl)acetic acid dimethylamide.
Yield: 38% of theory,
Melting point: 229° C. (decomp.)

| Calculated: | C 70.84 | H 7.93 | N 5.51 |
|---|---|---|---|
| Found: | 70.75 | 7.83 | 5.64 |

EXAMPLE 64

4-(3-(3-(5-Dimethylamino-5-oxo-pent-1-yl)piperidin-1-yl)-prop-1-yl)-[2.2]paracyclophane-oxalate Prepared analogously to Example 1 from 4-(3-bromoprop-1-yl)-[2.2]paracyclophane and 5-(piperidin-3-yl)pentanoic acid dimethylamide.
Yield: 54% of theory,
Melting point: 160° C.

| Calculated: | C 71.97 | H 8.42 | N 5.09 |
|---|---|---|---|
| Found: | 71.79 | 8.37 | 5.04 |

EXAMPLE 65

4-(3-(3-(3-Amino-3-oxo-prop-1-yl)piperidin-1-yl)prop-1-yl)-[2.2]paracyclophane-oxalate Prepared analogously to Example 1 from 4-(3-bromoprop-1-yl)-[2.2]paracyclophane and 3-(piperidin-3-yl)propionic acid amide.
Yield: 50% of theory,
Melting point: 186° C.

| Calculated: | C 70.42 | H 7.74 | N 5.66 |
|---|---|---|---|
| Found: | 70.52 | 8.07 | 5.71 |

EXAMPLE 66

4-(3-(4-Carboxy-piperidin-1-yl)prop-1-yl)-[2.2]paracyclophane sodium salt

Prepared analogously to Example 3 from 4-(3-(4-ethoxycarbonyl-piperidin-1-yl)prop-1-yl)-[ 2.2]paracyclophane and sodium hydroxide solution.
Yield: 68% of theory,
Melting point: about 280° C.

| Calculated: | C 75.16 | H 7.57 | N 3.51 |
|---|---|---|---|
| Found: | 74.97 | 7.77 | 3.77 |

EXAMPLE 67

4-(3-(4-(Dimethylaminocarbonyl)piperidin-1-yl)prop-1-yl)-[2.2]paracyclophane-oxalate Prepared analogously to Example 1 from 4-(3-bromoprop-1-yl)-[2.2]paracyclophane and (piperidin-4-yl)carboxylic acid dimethylamide.
Yield: 36% of theory,
Melting point: 170° C. (decomp.)

| | | | |
|---|---|---|---|
| Calculated: | C 70.42 | H 7.74 | N 5.66 |
| Found. | 70.27 | 7.79 | 5.69 |

EXAMPLE 68

4-(3-(3-(Dimethylaminocarbonyl)piperidin-1-yl)prop-1-yl)-[2.2]paracyclophane-oxalate Prepared analogously to Example 1 from 4-(3-bromoprop-1-yl)-[2.2]paracyclophane and (piperidin-3-yl)carboxylic acid dimethylamide.
Yield: 23% of theory,
Melting point: 140° C.

| | | | |
|---|---|---|---|
| Calculated: | C 70.42 | H 7.74 | N 5.66 |
| Found: | 70.26 | 7.72 | 5.73 |

EXAMPLE 69

4-(3-(3-(2-Carboxy-eth-1-yl)piperidin-1-yl)prop-1-yl)-[2.2]paracyclophane-sodium salt Prepared analogously to Example 3 from 4-(3-(3-(2-ethoxycarbonyl-eth-1-yl)piperidin-1-yl)prop-1-yl)-[2.2]paracyclophane and sodium hydroxide solution.
Yield: 80% of theory,
Melting point: 262° C.

| | | | |
|---|---|---|---|
| Calculated: | C 75.84 | H 8.02 | N 3.28 |
| Found: | 75.66 | 8.13 | 3.18 |

EXAMPLE 70

4-(3-(3-(3-Dimethylamino-3-oxo-prop-1-yl)piperidin-1-yl)prop-1-yl)-[2.2]paracyclophane-oxalate Prepared analogously to Example 1 from 4-(3-bromoprop-1-yl)-[2.2]paracyclophane and 3-(piperidin-3-yl)propionic acid dimethylamide.
Yield: 43% of theory,
Melting point: 146° C.

| | | | |
|---|---|---|---|
| Calculated: | C 71.24 | H 8.10 | N 5.36 |
| Found: | 71.07 | 8.08 | 5.56 |

EXAMPLE 71

4-Methanesulphonyloxy-7-(3-(piperidin-1-yl)prop-b 1-yl)-[2.2]paracyclophane-oxalate Prepared analogously to Example 7 from 4-hydroxy-7-(3-(piperidin-1-yl)prop-1-yl)-[2.2]paracyclophane and methanesulphonic acid chloride.
Yield: 30% of theory,
Melting point: 191° C.

| | | | | |
|---|---|---|---|---|
| Calculated: | C 62.65 | H 6.82 | N 2.71 | S 6.19 |
| Found: | 62.52 | 6.83 | 2.69 | 6.43 |

EXAMPLE 72

4-Methoxy-7-(3-(piperidin-1-yl)prop-1-yl)-[2.2]paracyclophane-hydrobromide

Prepared analogously to Example 1 from 4-methoxy-7-(3-bromoprop-1-yl)-[2.2]paracyclophane and piperidine.
Yield: 63% of theory,
Melting Point: 196°-197° C.

| | | | | |
|---|---|---|---|---|
| Calculated: | C 67.56 | H 7.71 | N 3.15 | Br 17.98 |
| Found: | 67.44 | 7.65 | 3.32 | 18.19 |

EXAMPLE 73

4-Methoxy-7-(3-(3-(N-acetyl-methylamino-methyl)-piperidin-1-yl)prop-1-yl)-[2.2]paracyclophane-oxalate Prepared analogously to Example 1 from 4-methoxy-7-(3-bromoprop-1-yl)-[2.2]paracyclophane and 3-(N-acetylmethylamino-methyl)-piperidine.
Yield: 60% of theory,
Melting point: 140°-143° C.

| | | | |
|---|---|---|---|
| Calculated: | C 69.12 | H 7.86 | N 5.20 |
| Found: | 69.31 | 7.71 | 5.10 |

EXAMPLE 74

4-Hydroxy-7-(3-(3-(N-acetyl-methylamino-methyl)-piperidin-1-yl)prop-1-yl)[2.2]paracyclophane-oxalate Prepared analogously to Example 1 from 4-hydroxy-7-(3-bromoprop-1-yl)-[2.2]paracyclophane and 3-(N-acetylmethylamino-methyl)-piperidine.
Yield: 60% of theory,
Melting point: 60° C. (decomp.)

| | | | |
|---|---|---|---|
| Calculated: | C 68.76 | H 7.69 | N 5.34 |
| Found: | 68.97 | 7.87 | 5.16 |

EXAMPLE 75

4-Hydroxy-7-(3-(piperidin-1-yl)prop-1-yl)-[2.2]paracyclophane

Prepared analogously to Example 1 from 4-hydroxy-7-(3-bromoprop-1-yl)-[2.2]paracyclophane and piperidine.
Yield: 63% of theory,
Melting point: 143°-145° C.

| | | | |
|---|---|---|---|
| Calculated: | C 82.47 | H 8.94 | N 4.01 |
| Found: | 82.23 | 8.99 | 4.10 |

EXAMPLE 76

4-Methyl-7-(3-(3-(N-acetyl-methylamino-methyl)-piperidin-1-yl)prop-1-yl)-[2.2]paracyclophane-oxalate Prepared analogously to Example 1 from 4-methyl-7-(3-bromoprop-1-yl)-[2.2]paracyclophane and 3-(N-acetylmethylamino-methyl)-piperidine.
Yield: 49% of theory,
Melting point: 153° C.

| Calculated: | C 71.24 | H 8.04 | N 5.36 |
|---|---|---|---|
| Found: | 71.07 | 8.23 | 5.27 |

EXAMPLE 77

4,5,12,13-Tetramethyl-7-(3-(3-(N-acetyl-methylamino-methyl)-piperidin-1-yl)prop-1-yl)-[2.2]paracyclophane-oxalate Prepared analogously to Example 1 from 4,5,12,13-tetramethyl-7-(3-bromoprop-1-yl)-[2.2]paracyclophane and 3-(N-acetyl-methylamino-methyl)piperidine.
Yield: 60% of theory,
Melting point: about 160° C

| Calculated: | C 72.31 | H 8.57 | N 4.96 |
|---|---|---|---|
| Found: | 72.17 | 8.74 | 5.02 |

EXAMPLE 78

4,5,12,13-Tetramethyl-7-(3-(3-(N-acetyl-methylaminomethyl)-piperidin-1-yl)prop-1-yl)-[2.2]paracyclophane-oxalate Prepared analogously to Example 1 from 4,5,12,13-tetramethyl-7-(3-bromoprop-1-yl)-[2.2]paracyclophane and 3-(N-acetyl-methylamino-methyl)piperidine.
Yield: 44% of theory,
Melting point: 178° C. (decomp.)

| Calculated: | C 72.31 | H 8.57 | N 4.96 |
|---|---|---|---|
| Found: | 72.13 | 8.74 | 4.87 |

EXAMPLE 79

(S)(+) 4-(3-(Piperidin-1-yl)prop-1-yl)-[2.2]paracyclophane-hydrochloride 3.3 g (0.01 mol) of 4-(3-(piperidin-1-yl)prop-1-yl)-[2.2]paracyclophane dissolved in 10 ml of ethanol are added to 1.50 g (0.01 mol) of L(+) tartaric acid in 60 ml of ethanol. The mixture is then refluxed for 5 minutes and cooled. The resulting precipitate is filtered off and recrystallised 4 times from 95% aqueous ethanol. The salt is then liberated with 2 molar sodium hydroxide solution and the free base is extracted 3 times with ethyl acetate. The organic phase is dried over sodium sulphate and concentrated by evaporation. The hydrochloride is precipitated from acetone using methanolic hydrochloric acid.
Yield: 0.70 g (42% of theory),
Melting point: 262° C.
$[\alpha]_D^{20} = +64°$ (c=0.70 in chloroform).

What is claimed is:
1. A cyclophane of the formula

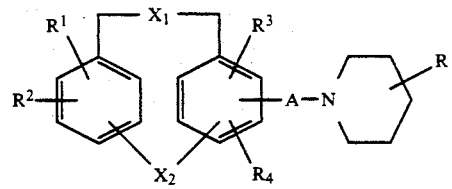

wherein
$X_1$ and $X_2$, which may be identical or different, each represent a straight-chained $C_{2-4}$-alkylene or alkenylene group,
A represents a straight-chained $C_{1-6}$-alkylene group, a $-Y_1-A_1-$ or $-Y_2-A_2-$ group, wherein
$Y_1$ represents an oxygen atom or a sulphenyl, sulphinyl or sulphonyl group,
$A_1$ represents a straight-chained $C_{2-4}$-alkylene group,
$Y_2$ represents an ethenylene or ethynylene group and
$A_2$ represents a straight-chained $C_{1-3}$-alkylene group,
wherein the groups $A_1$ and $A_2$ are linked to the piperidinyl moiety and the carbon structure of the groups A, $A_1$ and $A_2$ may additionally be substituted by one or two methyl groups,
$R_1$, $R_2$, $R_3$ and $R_4$, which may be identical or different, each represent a hydrogen or halogen atom or an alkyl, hydroxy, alkoxy or alkylsulphonyloxy group each having 1 to 3 carbon atoms in the alkyl part; and
R represents a hydrogen, hydroxy, alkoxy, carboxy, alkoxycarbonyl, aminocarbonyl, alkylaminocarbonyl or dialkylaminocarbonyl group or a $C_{1-5}$ alkyl group which may be substituted by a hydroxy, alkoxy, alkanoyloxy, cyano, carboxy, alkoxycarbonyl, aminocarbonyl, alkylaminocarbonyl, dialkylaminocarbonyl, amino, alkylamino, dialkylamino, alkanoylamino, alkylsulphonylamino, N-alkanoylalkylamino or N-alkylsulphonylalkylamino group, wherein, unless otherwise specified, the alkyl, alkoxy and alkanoyl moieties may each contain 1 to 3 carbon atoms,
the enantiomers, diastereomers or addition salts thereof.
2. A cyclophane of the formula

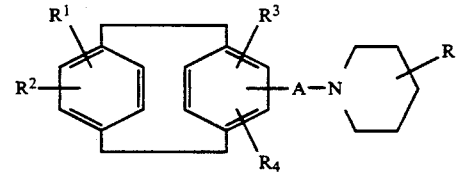

wherein
A represents a straight-chained $C_{1-5}$-alkylene group, a $-Y_1-A_1-$ or $-Y_2-A_2-$ group, wherein
$Y_1$ represents an oxygen atom,
$A_1$ represents a straight-chained $C_2$ or $C_3$-alkylene group,
$Y_2$ represents an ethenylene or ethynylene group and
$A_2$ represents a methylene group,
the groups $A_1$ and $A_2$ being linked to the piperidinyl moiety, $R_1$, $R_2$, $R_3$ and $R_4$ represents a hydrogen, fluorine, chlorine or bromine atom or a methyl, hydroxy, methoxy or methanesulphonyloxy group and the other groups $R_1$, $R_2$, $R_3$ or $R_4$ each represent a hydrogen group or a methyl group, and R represents a carboxy, ethoxycarbonyl, aminocarbonyl, methylaminocarbonyl or dimethylaminocarbonyl group or a methyl group substituted by a hydroxy, acetoxy, cyano, carboxy, ethoxycarbonyl, aminocarbonyl, methylaminocarbonyl, dimethylaminocarbonyl, amino, methylamino, dimethylamino, diethylamino, acetylamino, N-acetylmethylamino, methanesulphonylamino or N-methanesulphonylmethylamino group or an ethyl group substituted in the 2-position by a hydroxy, carboxy or ethoxycarbonyl groups or a $C_{2-4}$-alkyl group substituted in the 2-, 3- or 4-position by a dimethylaminocarbonyl group, the enantiomers, diastereomers or addition salts thereof.

3. A cyclophane as recited in claim 2, wherein
A represents a straight-chained $C_{2-4}$-alkylene group,
a $-Y_1-A_1-$ or $-Y_2-A_2-$ group, wherein
$Y_1$ represents an oxygen atom
$A_1$ represents a straight-chained $C_2$ or $C_3$-alkylene group,
$Y_2$ represents an ethenylene or ethynylene group and
$A_2$ represents a methylene group, the groups $A_1$ and $A_2$ being linked to the piperidinyl moiety,
$R_1$, $R_2$, $R_3$ and $R_4$ each represent a hydrogen atom and
R represents a carboxy, ethoxycarbonyl, aminocarbonyl, methylaminocarbonyl or dimethylaminocarbonyl group or a methyl group substituted by hydroxy, acetoxy, cyano, carboxy, ethoxycarbonyl, aminocarbonyl, methylaminocarbonyl, dimethylaminocarbonyl, amino, methylamino, dimethylamino, diethylamino, acetylamino, N-acetylmethylamino, methanesulphonylamino or N-methane-sulphonylmethylamino or an ethyl group substituted in the 2-position by a hydroxy, carboxy or ethoxycarbonyl group, or a $C_{2-4}$-alkyl group substituted in the 2-, 3- or 4-position by a dimethylaminocarbonyl group, the enantiomers, diastereomers or addition salts thereof.

4. A cyclophane as recited in claim 2 selected from the group consisting of:
4-(3-(piperidin-1-yl)prop-1-yl)-[2.2]paracyclophane,
4-(3-(3-(N-acetyl-methylaminomethyl)piperidin-1-yl)prop-1-yl)-[2.2]paracyclophane,
4-methyl-7-(3-(3-(N-acetyl-methylaminomethyl)-piperidin-1-yl)-prop-1-yl)[2.2]paracyclophane,
4-(3-(3-(3-dimethylamino-3-oxo-prop-1-yl)piperidin-1-yl)-prop-1-yl)-[2.2]paracyclophane and
4-(2-(piperidin-1-yl)ethoxy-[2.2]paracyclophane,
the enantiomers, diastereomers and addition salts thereof.

5. A physiologically acceptable acid addition salt of the cyclophane as recited in claim 1 with an organic or inorganic acid.

6. A physiologically acceptable acid addition salt of the cyclophane as recited in claim 2 with an organic or inorganic acid.

7. A physiologically acceptable acid addition salt of the cyclophane as recited in claim 3 with an organic or inorganic acid.

8. A physiologically acceptable acid addition salt of the cyclophane as recited in claim 4 with an organic or inorganic acid.

9. A pharmaceutical composition useful in the treatment of hypertension comprising a therapeutically effective amount of a cyclophane as recited in claim 1 or a physiologically acceptable acid addition salt thereof, and one or more carriers or diluents.

10. A pharmaceutical composition useful in the treatment of hypertension comprising a therapeutically effective amount of a cyclophane as recited in claim 2 or a physiologically acceptable acid addition salt thereof, and one or more carriers or diluents.

11. A pharmaceutical composition useful in the treatment of hypertension comprising a therapeutically effective amount of a cyclophane as recited in claim 3 or a physiologically acceptable acid addition salt thereof, and one or more carriers or diluents.

12. A pharmaceutical composition useful in the treatment of hypertension comprising a therapeutically effective amount of a cyclophane as recited in claim 4 or a physiologically acceptable acid addition salt thereof, and one or more carriers or diluents.

13. A method for the treatment of hypertension in a patient, which comprises administering to the patient a therapeutically effective amount of a cyclophane as recited in claim 1.

14. A method for the treatment of hypertension in a patient, which comprises administering to the patient a therapeutically effective amount of a cyclophane as recited in claim 2.

15. A method for the treatment of hypertension in a patient, which comprises administering to the patient a therapeutically effective amount of a cyclophane as recited in claim 3.

16. A method for the treatment of hypertension in a patient, which comprises administering to the patient a therapeutically effective amount of a cyclophane as recited in claim 4.

* * * * *